United States Patent
Schneider et al.

(10) Patent No.: US 9,801,763 B2
(45) Date of Patent: Oct. 31, 2017

(54) METHOD AND APPARATUS FOR ADVANCING AN ABSORBENT ARTICLE

(71) Applicant: The Procter & Gamble Company, Cincinnati, OH (US)

(72) Inventors: Uwe Schneider, Cincinnati, OH (US); Todd Douglas Lenser, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/582,812

(22) Filed: May 1, 2017

(65) Prior Publication Data

US 2017/0231830 A1    Aug. 17, 2017

Related U.S. Application Data

(63) Continuation of application No. 14/038,828, filed on Sep. 27, 2013.

(Continued)

(51) Int. Cl.

| B65G 47/24 | (2006.01) |
|---|---|
| B32B 37/22 | (2006.01) |
| A61F 13/15 | (2006.01) |
| B65G 37/00 | (2006.01) |
| B65G 47/244 | (2006.01) |

(52) U.S. Cl.
CPC .. *A61F 13/15764* (2013.01); *A61F 13/15585* (2013.01); *A61F 13/15772* (2013.01); *B65G 37/00* (2013.01); *B65G 47/244* (2013.01); *A61F 2013/16* (2013.01)

(58) Field of Classification Search
CPC   A61F 13/15764; B31F 1/0006; B65G 47/244
USPC ..... 198/377.02, 377.04, 408, 411, 412, 416; 493/405, 413, 418
See application file for complete search history.

(56) References Cited

U.S. PATENT DOCUMENTS

| 3,994,486 A | * | 11/1976 | Nystrand | .......... A61F 13/15747 493/427 |
|---|---|---|---|---|
| 4,029,310 A | * | 6/1977 | Reist | ...................... B65H 29/28 493/426 |

(Continued)

FOREIGN PATENT DOCUMENTS

JP    2012-024242 A    2/2012

*Primary Examiner* — Douglas Hess
(74) *Attorney, Agent, or Firm* — Sarah M. DeCristofaro

(57) ABSTRACT

A converting apparatus operates to transfer a folded absorbent article from a first carrier apparatus to a second carrier apparatus. The converting apparatus includes a transfer apparatus and a guide member located adjacent to the transfer apparatus, forming a gap there between. The transfer apparatus includes a frame that is rotatable about a first axis of rotation and a transfer member that is rotatable about a second axis of rotation. The transfer member defines a receiving surface and the guide member defines a guide surface. The guide surface converges toward the receiving surface. The frame advances the absorbent article in a machine direction through the gap. While advancing absorbent article advances through the gap, the transfer member rotates the absorbent article about the second axis of rotation. The guide member includes side seam tuckers that are adapted to tuck the side seams of the absorbent article.

20 Claims, 19 Drawing Sheets

Related U.S. Application Data

(60) Provisional application No. 61/717,282, filed on Oct. 23, 2012.

(56) References Cited

U.S. PATENT DOCUMENTS

| | | | | |
|---|---|---|---|---|
| 5,176,615 A * | 1/1993 | Munsch | ............ | A61F 13/15747 493/427 |
| 5,224,405 A * | 7/1993 | Pohjola | ............. | A61F 13/15756 156/519 |
| 6,497,032 B2 * | 12/2002 | Maxton | ............ | A61F 13/15764 156/226 |
| 7,322,925 B2 * | 1/2008 | Couillard | .......... | A61F 13/15772 493/394 |
| 8,011,493 B2 * | 9/2011 | Giuliani | ............... | B65G 47/244 198/406 |
| 8,556,790 B2 * | 10/2013 | Fujita | ................ | A61F 13/15747 493/357 |
| 8,617,341 B2 * | 12/2013 | Schneider | ......... | A61F 13/15747 156/196 |
| 9,017,241 B2 * | 4/2015 | Lavon | ................ | A61F 13/15747 493/405 |
| 9,266,314 B2 * | 2/2016 | Findley | ............. | A61F 13/15764 |
| 9,572,723 B2 * | 2/2017 | Schneider | ......... | A61F 13/15764 |
| 2015/0202093 A1 | 7/2015 | LaVon et al. | | |

* cited by examiner

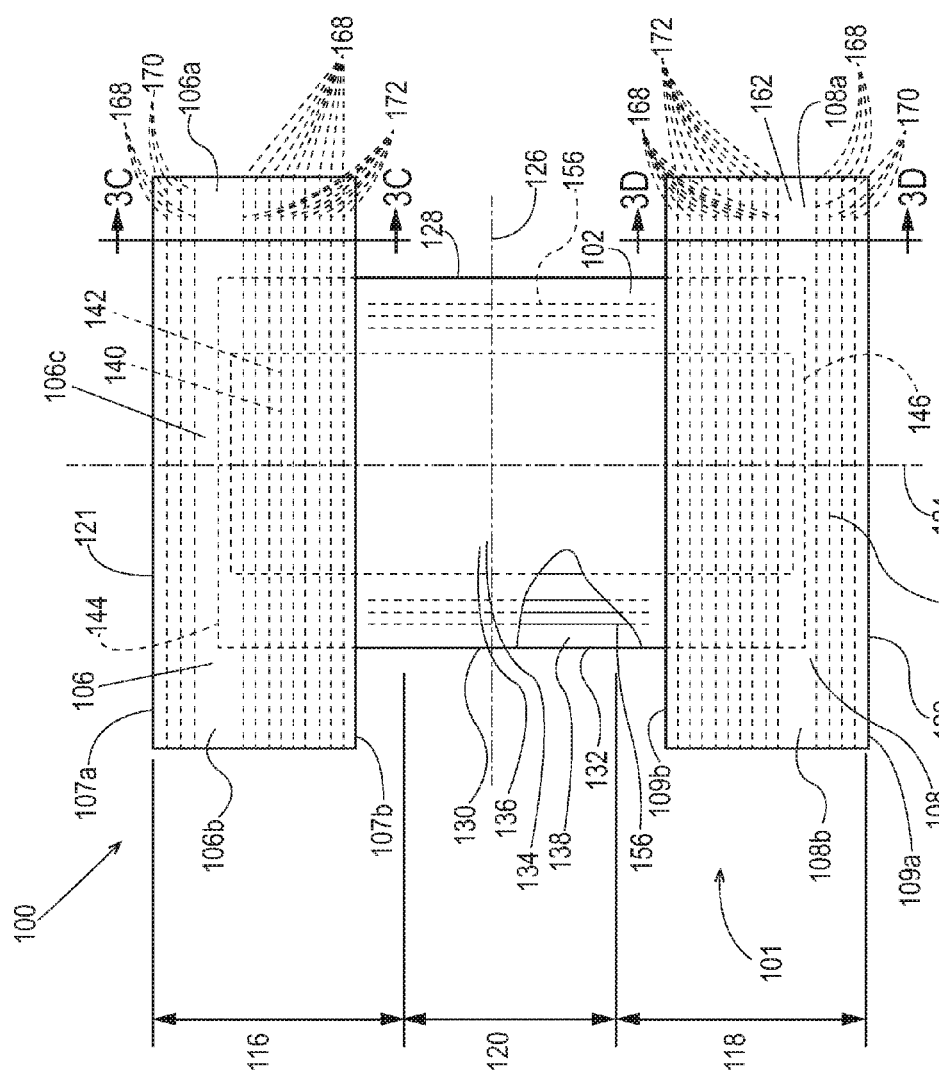

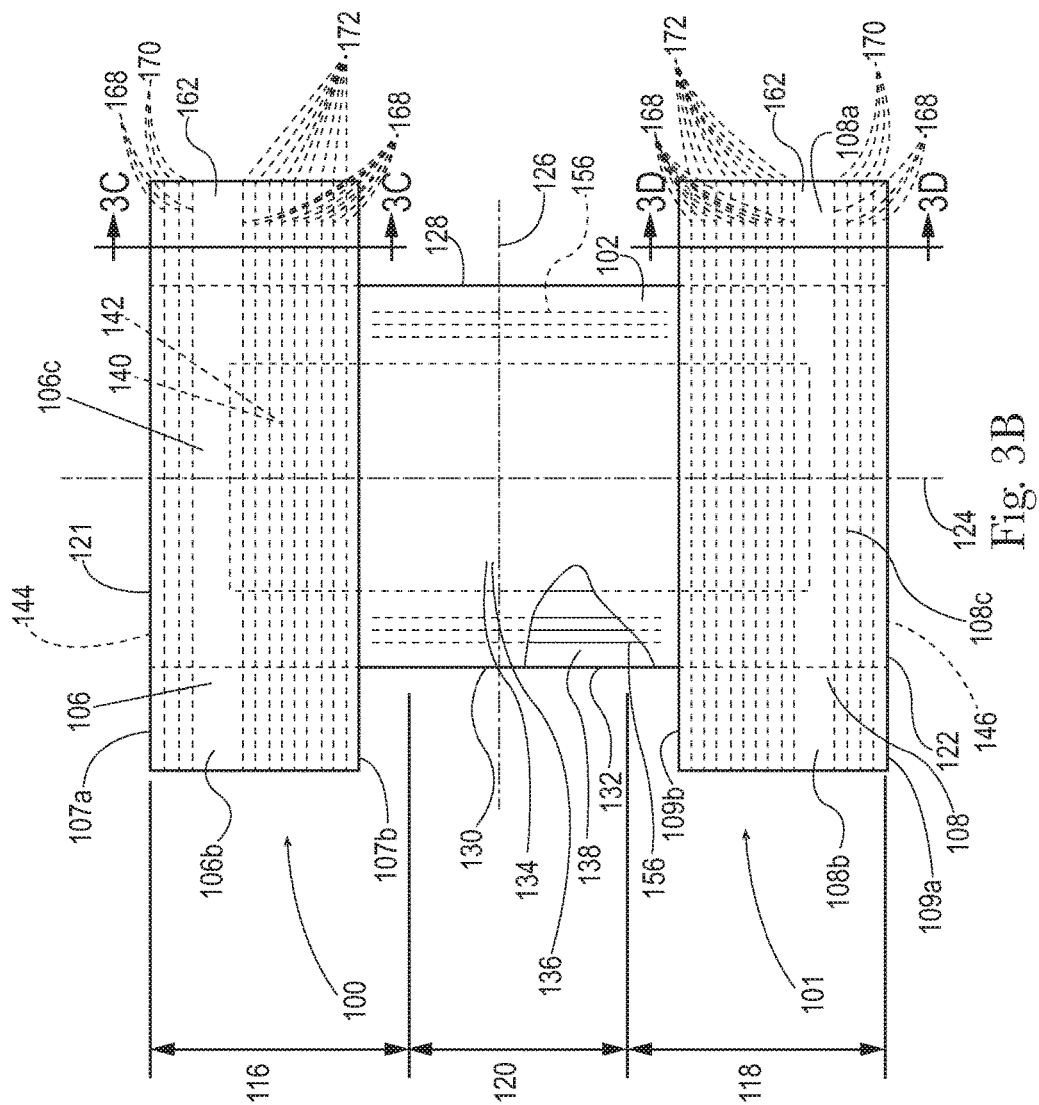

METHOD AND APPARATUS FOR ADVANCING AN ABSORBENT ARTICLE

FIELD OF THE INVENTION

The present disclosure relates to methods and apparatuses for manufacturing absorbent articles, and more particularly, methods and apparatuses for advancing an absorbent article.

BACKGROUND OF THE INVENTION

Along an assembly line, various types of articles, such as, diapers, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing webs and component parts are subjected to a final knife cut to separate the webs into discrete diapers or other absorbent articles.

After the final knife cut, absorbent articles may undergo a folding process to bring front and rear waist regions together. In some processes, the folded absorbent articles may be rotated prior to packaging. For example, in some processes, the folded absorbent article may advance in a sideways orientation and may be rotated about 90 degrees to a desired orientation for packaging. Some processes for rotating a folded absorbent article 10 may hold the front waist region 12 of the absorbent article 10 while the rear waist region 14 is unrestricted from movement, such as shown in FIG. 1. Other processes may hold the rear waist region 14 of the folded absorbent article 10, while the front waist region 12 is unrestricted from movement. The process of rotating the folded absorbent article 10 may subject the folded absorbent article 10 to centrifugal and/or gravitational forces. As a result, the unrestricted rear waist region 14 of the folded absorbent article 10 may be pulled away from the front waist region 12. Consequently, an absorbent article 10 that is not fully folded, such as instances where the front waist region 12 is not contacting the rear waist region 14, may get stuck in downstream processing and/or may cause the folded absorbent articles 10 to be improperly packaged. In some processes, conveyors or belts may be used to control the movement of the unrestricted waist region. However, friction between the belt or conveyor and the absorbent article 10 may impede the advancement of the folded absorbent article 10. Therefore, it would be beneficial to provide a process and apparatus for guiding a folded absorbent article without also impeding the advancement of the folded absorbent article.

In some processes, opposing side seams of a folded absorbent article may be tucked into the chassis of the absorbent article prior to packaging. Some processes for tucking side seams may utilize vacuum conveyor belts to hold the front and rear waist regions of the folded absorbent article apart from each other as side seam tuckers tuck the side seams into the chassis. However, subjecting the folded absorbent article to multiple, discrete processing steps prior to packaging, such as rotating and reorienting the absorbent article and then subsequently tucking the side seams, adds cost and complexity to the manufacturing process. Therefore, it would be beneficial to provide a single process and apparatus for rotating and tucking side seams of a folded absorbent article.

SUMMARY OF THE INVENTION

Aspects of the present disclosure may include a method of transferring discrete absorbent articles from a first carrier apparatus to a second carrier apparatus. Each absorbent article comprises a first waist region and a second waist region separated by a crotch region. The method comprises the steps of: advancing an absorbent article with the first carrier apparatus in a machine direction to a transfer apparatus, the transfer apparatus comprising a transfer member, the transfer member having a receiving surface, wherein the transfer member is connected with a frame, wherein a guide member is located adjacent to the transfer apparatus, the guide member having a guide surface that is in a facing relationship with the receiving surface; transferring the absorbent article from the first carrier apparatus to the transfer member, wherein the first waist region is positioned on the receiving surface; advancing the absorbent article between the receiving surface and the guide surface by rotating the frame about a first axis of rotation; rotating the transfer member about a second axis of rotation as the transfer apparatus rotates about the first axis of rotation, wherein the second axis of rotation is orthogonal to the first axis of rotation; applying a positive air pressure from the guide surface to the second waist region of the absorbent article as the absorbent article advances between the receiving surface and the guide surface; and transferring the absorbent article from the transfer apparatus to the second carrier apparatus.

Aspects of the present disclosure may include a method for advancing an absorbent article, the method comprising the steps of: advancing an absorbent article in a machine direction to a transfer apparatus, the absorbent article having a first waist region and a second waist region separated by a crotch region, wherein absorbent article is folded such that the first waist region is in a facing relationship with the second waist region, wherein the transfer apparatus comprises a frame, a transfer member, and a guide member, wherein the transfer member has a receiving surface, wherein the guide member has a guide surface; advancing an absorbent article onto the receiving surface of the transfer member; rotating the frame about a first axis of rotation to advance the absorbent article between the receiving surface and the guide surface; separating the second waist region from the first waist region with centrifugal force; tucking the side seams between the separated first and second waist regions; and guiding the first waist region with the guide surface into contact with the second waist region.

Aspects of the present disclosure may include an apparatus for controlling an absorbent advancing in a machine direction. The apparatus comprises a frame rotatable about a first axis of rotation. The apparatus comprises a transfer member connected with the frame. The transfer member has a receiving surface. The apparatus includes a guide member having a guide surface, and having a first end portion and a second end portion. The guide member is positioned adjacent to frame so as to define a gap between the receiving surface and the guide surface. The gap defines a first distance between the first end portion of the guide surface and the receiving surface. The second distance is less than the first distance. The apparatus comprises a side seam tucker located adjacent to the receiving surface.

BRIEF DESCRIPTION OF THE DRAWINGS

FIG. 3A is a partially cut-away, plan view of a diaper pant.

FIG. 3B is a partially cut-away, plan view of a diaper pant.

DETAILED DESCRIPTION OF THE INVENTION

Figure 1:
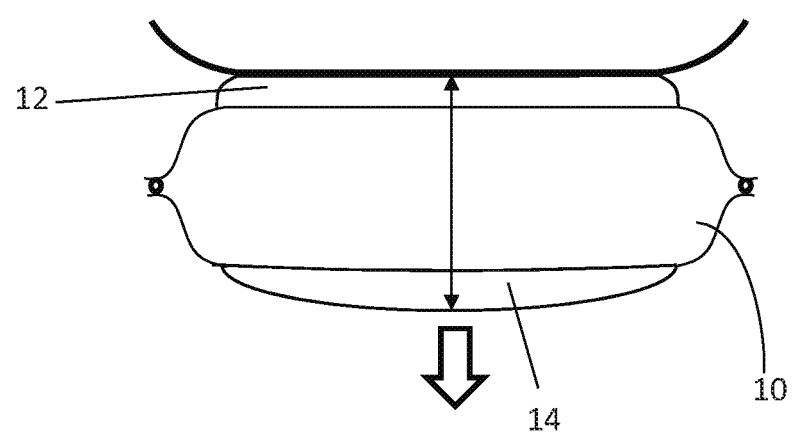
FIG. 1 is a schematic, sectional view of a folded diaper pant subjected to gravitational and/or centrifugal forces according to prior art methods.

The following definitions may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

"Joined" is used herein to encompass configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Substrate" is used herein to describe a material which is primarily two-dimensional (i.e. in an XY plane) and whose thickness (in a Z direction) is relatively small (i.e. 1/10 or less) in comparison to the substrate's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

"Nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

"Machine direction" (MD) is used herein to refer to the direction of material flow through a process. In addition, relative placement and movement of material can be described as flowing in the machine direction through a process from upstream in the process to downstream in the process.

"Cross direction" (CD) is used herein to refer to a direction that is not parallel with, and usually perpendicular to, the machine direction.

"Pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. As discussed in more detail below, a diaper pant can be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers can be preformed anywhere along the circumference of the waist region (e.g., side fastened or connected, front waist fastened or connected, rear waist fastened or connected).

Aspects of the present disclosure involve methods and apparatuses for manufacturing absorbent articles, and more particularly, methods and apparatuses for controlling an advancing folded absorbent article. As discussed in more detail below, in a converting process, folded absorbent articles may be transferred onto a transfer apparatus. The transfer apparatus may be adapted to rotate and reorient the folded absorbent articles. During the rotating and reorienting process, the folded absorbent articles may be subjected to centrifugal and/or gravitational forces. The converting apparatus may include a guide member that is located adjacent to the transfer apparatus and that is configured to control the movement of the advancing, folded absorbent articles. In addition, the guide member may be configured to perform a side seam tucking operation while the folded absorbent articles are advancing on the transfer apparatus.

The folded discrete absorbent article may include a chassis having longitudinally opposing first waist and second waist regions separated by a crotch region. The discrete absorbent article may be folded in a U-shape to bring the first waist region into a facing relationship with the second waist region. A ring-like elastic belt may connect the first waist region and the second waist region. The ring-like elastic belt may include a first elastic belt and a second elastic belt. The first and second elastic belts may each be defined by a first end region and a second end region laterally separated by a central region. The first end regions of the first and second elastic belts may be joined to form a first side seam and the second end regions of the first and second elastic belts may be joined to form a second side seam.

A converting apparatus of the present disclosure includes a transfer apparatus for advancing a folded absorbent article from a first carrier apparatus to a second carrier apparatus. The transfer apparatus includes a frame and a plurality of transfer members rotatably connected with the frame. The frame is rotatable about a first axis of rotation and the transfer members are rotatable about a second axis of rotation. The first axis of rotation extends in a different direction than the second axis of rotation. The first axis of rotation may be orthogonal to the second axis of rotation. The transfer members may define a receiving surface. The converting apparatus also includes a guide member located adjacent to the frame and forming a gap there between. The guide member may include a guide surface that is in a facing relationship with a receiving surface of the transfer member.

In operation, the first waist region of the folded absorbent article may be transferred from the first carrier apparatus to the transfer apparatus. The folded absorbent article may advance onto the receiving surface of the transfer member. The transfer apparatus advances the folded absorbent article in a machine direction about the first axis of rotation. The transfer member may concurrently rotate the folded absorbent article about the second axis of rotation. The transfer apparatus advances the folded absorbent article through a gap between the receiving surface and the guide surface. The folded absorbent article then advances from the transfer apparatus to the second carrier apparatus.

The guide member operates to limit movement of the second waist region caused by centrifugal and/or gravitational forces that may act on the advancing folded absorbent article as the absorbent articles advance in the machine direction about the first axis of rotation. It is to be appreciated that limiting the movement of the second waist region may assist the absorbent article in advancing to the second carrier apparatus while also controlling the desired orientation of the folded absorbent article for a downstream packaging operation.

In some exemplary configurations, the guide surface of the guide member may have a curved shape that corresponds with the curved shape of the receiving surface. In addition, the guide surface may converge toward the receiving surface of the transfer member as the folded absorbent article advances in the machine direction. More particularly, the gap between the guide surface and the receiving surface may be defined by a minimum distance. In some exemplary configurations, the gap may define a first distance at a first end portion of the guide member and second distance at a second end portion of the guide member. The second distance is shorter than the first distance. As a result, the guide member may guide the first and second waist regions of the folded absorbent article together in a fully folded configuration. The guide surface may be configured such that the coefficient of friction between the guide surface and the folded absorbent article is relatively low in order to assist the folded absorbent article in advancing in the machine direction.

In some exemplary configurations, a tucking process may be used along with the methods and apparatuses disclosed herein. For example, portions of the first and second end regions of the first and second elastic belts, including the first and second side seams, may be tucked into the chassis of the absorbent article as the absorbent advances through the gap between the transfer member and the guide member. As the second waist region is pulled away from the first waist region by centrifugal and/or gravitational force, a side seam tucker is adapted to tuck the side seams into the chassis. As the minimum distance of the gap decreases, the second waist region is brought toward the first waist region. Bringing the first waist region toward the second waist region may hold assist in holding the first and second side seams tucked into the chassis.

As previously mentioned, the processes and apparatuses discussed herein may be used to guide an advancing, folded absorbent article. To help provide additional context to the subsequent discussion, the following provides a general description of absorbent articles in the form of diaper pants that may be guided in accordance with the methods and apparatuses disclosed herein. While the present disclosure relates to advancing absorbent articles in the form of diapers pants, it is to be appreciated that the methods and apparatuses disclosed herein may be used with various types of absorbent articles in folded or unfolded configurations. Furthermore, the methods and apparatuses disclosed herein may be used to guide partially assembled diaper components and/or diaper chassis in a variety of converting operations.

Figure 2:
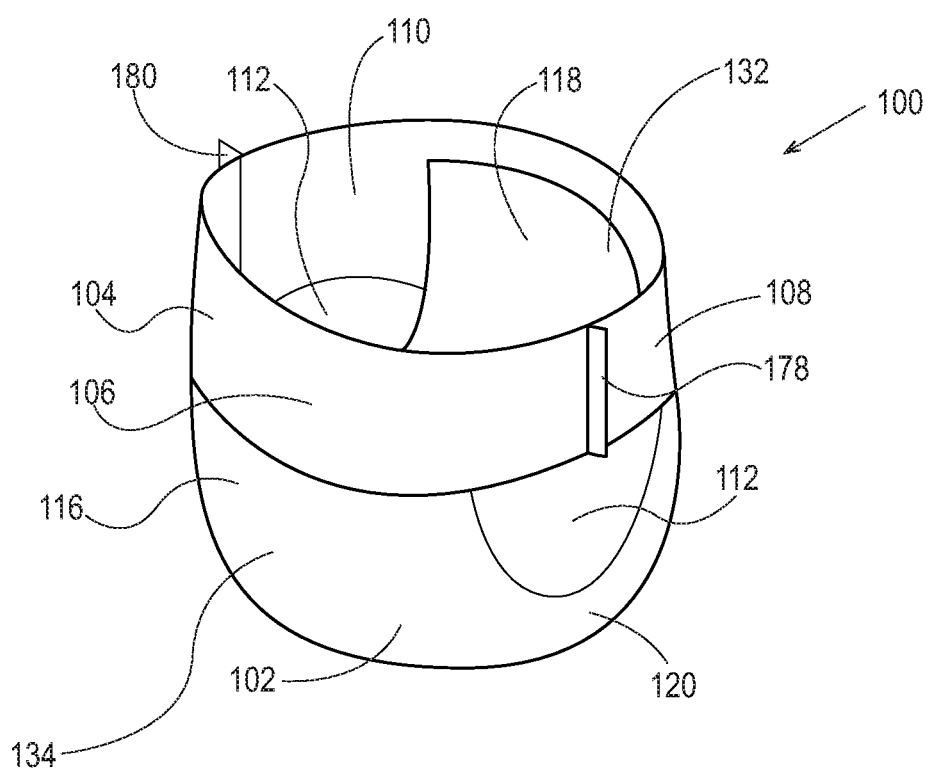
FIG. 2 is a schematic, perspective view of a diaper pant.

FIGS. 2 and 3A show an example of a diaper pant 100 that may be assembled and folded in accordance with the apparatuses and methods disclosed herein. In particular, FIG. 2 shows a perspective view of a diaper pant 100 in a pre-fastened configuration and FIG. 3A shows a plan view of the diaper pant 100 with the portion of the diaper that faces away from a wearer oriented toward the viewer. The diaper pant 100 shown in FIGS. 2 and 3A includes a chassis 102 and a ring-like elastic belt 104. As discussed below in more detail, a first elastic belt 106 and a second elastic belt 108 are connected together to form the ring-like elastic belt 104.

With continued reference to FIG. 3A, the chassis 102 includes a first waist region 116, a second waist region 118, and a crotch region 120 disposed intermediate the first and second waist regions. The first waist region 116 may be configured as a front waist region, and the second waist region 118 may be configured as back waist region. In some embodiments, the length of each of the front waist region 116, back waist region 118, and crotch region 120 may be one-third of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 3A are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 2 and 3A, the diaper pant 100 may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 3A, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 3A, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

Referring to FIG. 3A, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. Patent Publication No. 2009/0312730.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants 100 may have a continuous perimeter waist opening 110 and continuous perimeter leg openings 112 such as shown in FIG. 2.

As previously mentioned, the ring-like elastic belt 104 is defined by a first elastic belt 106 connected with a second elastic belt 108. As shown in FIG. 3A, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 2, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

Figure 3C:
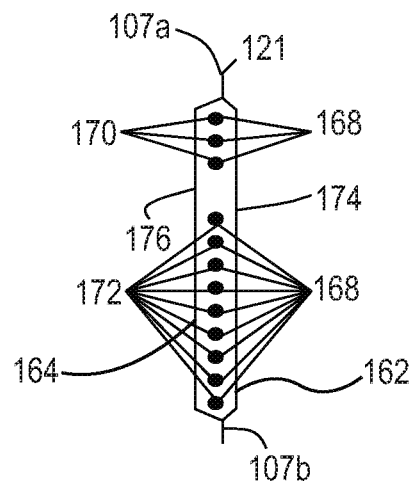
FIG. 3C is a cross-sectional view of the diaper pants of FIGS. 3A and 3B taken along line 3C-3C.
Figure 3D:
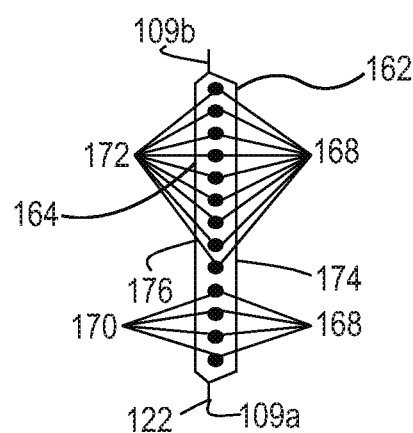
FIG. 3D is a cross-sectional view of the diaper pants of FIGS. 3A and 3B taken along line 3D-3D.

Referring to FIGS. 3A, 3C, and 3D, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt 106 and the second elastic belt 108 may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 3A, 3C, and 3D, the belt elastic material may include a plurality of elastic strands 168 which may be referred to herein as outer, waist elastics 170 and inner, waist elastics 172. As shown in FIG. 3A, the elastic strands 168 continuously extend laterally between the first and second opposing end regions 106a, 106b of the first elastic belt 106 and between the first and second opposing end regions 108a, 108b of the second elastic belt 108. In some embodiments, some elastic strands 168 may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt.

It is to be appreciated that the chassis 102 and elastic belts 106, 108 may be configured in different ways other than as depicted in FIG. 3A. For example, FIG. 3B shows a plan view of a diaper pant 100 having the same components as described above with reference to FIG. 3A, except the first laterally extending end edge 144 of the chassis 102 is aligned along and coincides with the outer lateral edge 107a of the first elastic belt 106, and the second laterally extending end edge 146 is aligned along and coincides with the outer lateral edge 109a of the second belt 108.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one exemplary configuration, a disposable absorbent article component comprises a bio-based content value from about 10% to about 100% using ASTM $D_{6866}$-10, method B, in another embodiment, from about 25% to about 75%, and in yet another embodiment, from about 50% to about 60% using ASTM $D_{6866}$-10, method B.

In order to apply the methodology of ASTM $D_{6866}$-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

Figure 4A:
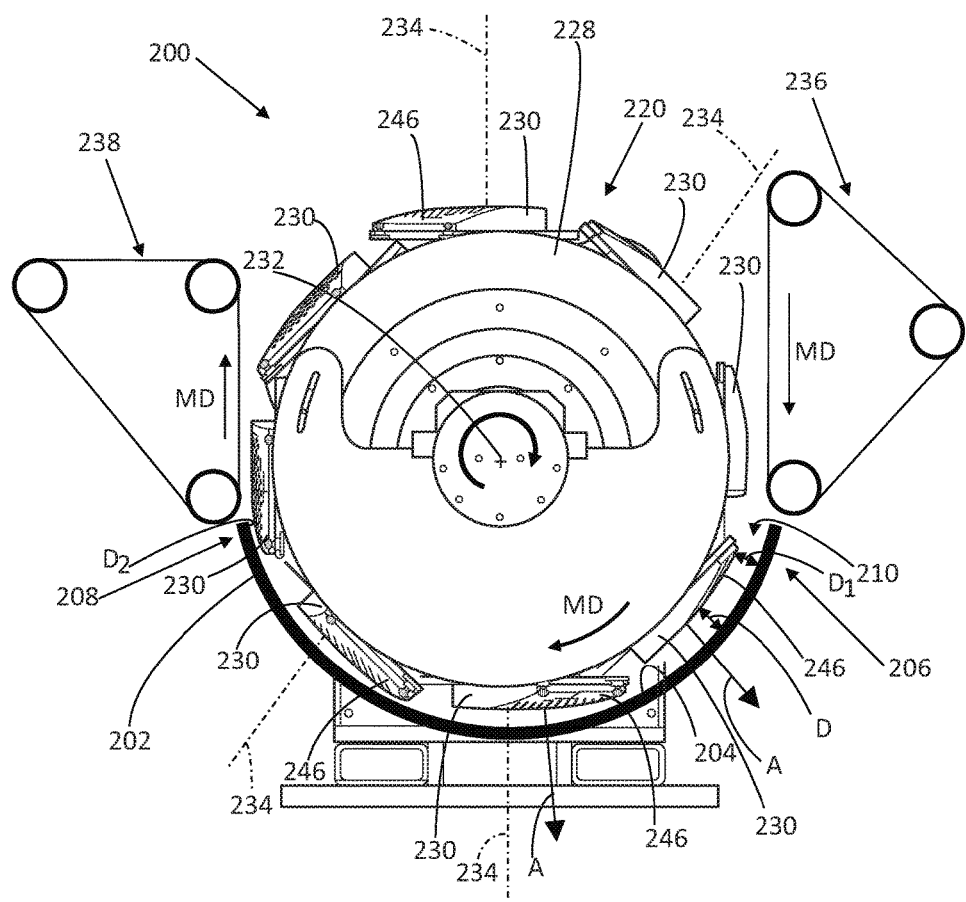
FIG. 4A is a schematic, side elevation view of a guide member locating adjacent to a transfer apparatus for guiding a folded diaper pant advancing in a machine direction.
Figure 4B:
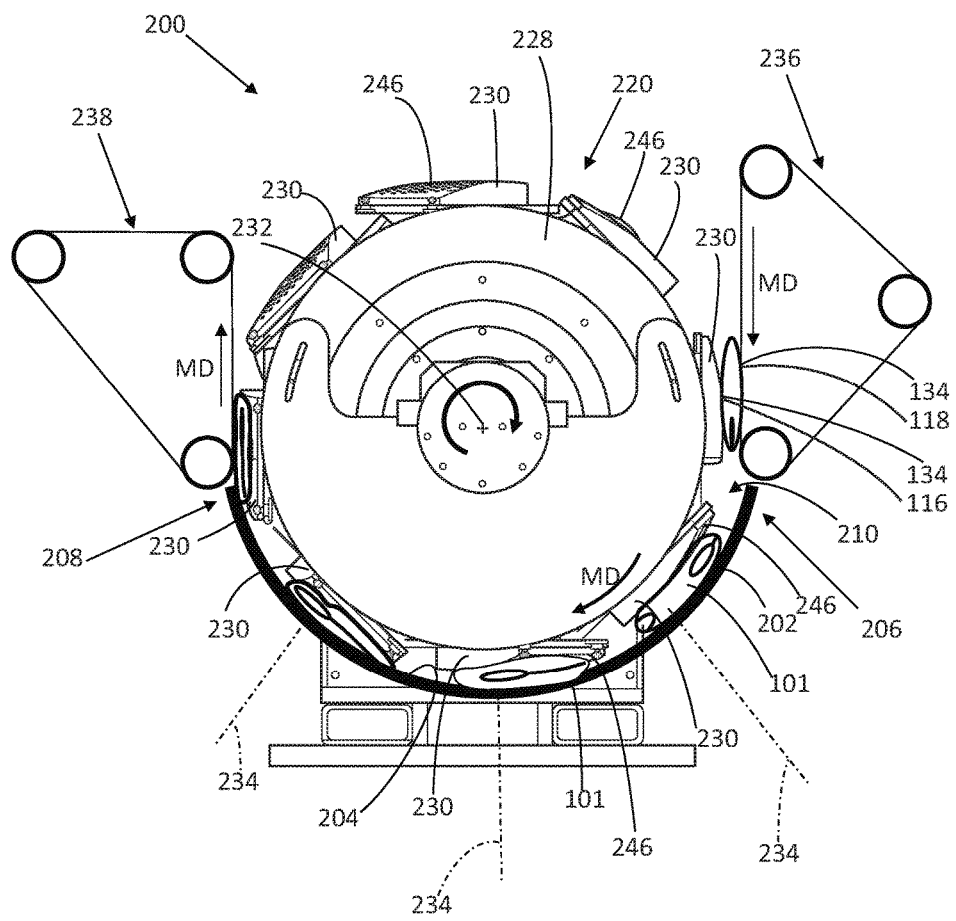
FIG. 4B is a schematic, side elevation view of a guide member locating adjacent to a transfer apparatus for guiding a folded diaper pant advancing in a machine direction.

As discussed above, the methods and apparatuses disclosed herein may be used to guide an advancing, folded diaper pant that is subjected to centrifugal and/or gravitational forces. FIGS. 4A and 4B show an exemplary converting apparatus 200 for guiding a folded diaper pant 101. The converting apparatus 200 includes a transfer apparatus 220 having a frame 228 and a plurality of transfer members 230 rotatably connected with the frame 228. The frame 228 may be configured to rotate about a first axis of rotation 232 and the transfer members 230 may be configured to concurrently rotate about a second axis of rotation 234 that extends in a different direction than the first axis of rotation 232. Each transfer member 230 is defined by a receiving surface 246. Exemplary transfer apparatuses are described in U.S. Pat. No. 9,150,321. The converting apparatus 200 includes a guide member 202 located adjacent to the frame 228 of the transfer apparatus 220 as to define a gap 210 there between. The guide member 202 includes a guide surface 204 that is positioned in a facing relationship with the receiving surfaces 246 of the transfer members 230. The converting apparatus 200 may include a first carrier apparatus 236 positioned adjacent to a first end portion 206 of the guide member 202 and a second carrier apparatus 238 positioned adjacent to a second end portion 208 of the guide member 202.

Referring to FIGS. 2, 4A, and 4B, in operation, a folded diaper pant 101 may advance in a machine direction MD onto the first carrier apparatus 236. The outer surface 134 of the second waist region 118 of the folded diaper pant 101 may contact the first carrier apparatus 236 and the outer surface 134 of the first waist region 116 may face away from the first carrier apparatus 236. It is to be appreciated that the folded diaper pants 101 may be subjected to various methods and apparatuses of assembly and construction between being received by the first carrier apparatus 236. Examples of such upstream processes and apparatuses are disclosed in U.S. Pat. No. 8,820,513; U.S. Pat. No. 8,607,959; U.S. Pat. No. 8,833,542; and U.S. Pat. No. 8,720,666.

It is to be appreciated that the first and second carrier apparatuses may be configured in various ways. For example, the first and second carrier apparatuses 236, 238 from and to which the diaper pants 101 are transferred may be rolls, drums, curved conveyors, linear conveyors, and/or discrete heads following a curvilinear path, for example. The first and second carrier apparatuses 236, 238 may be moving at a different surface velocity or at the same surface velocity. The transfer apparatus 220 may pick up the folded diaper pant 101 from the first carrier apparatus 236 at the same velocity as is applied to the folded diaper pant 101 at the second carrier apparatus 238.

From the first carrier apparatus 236, the outer surface 134 of the first waist region 116 of the folded diaper pant 101 may advance onto a receiving surface 246 of a transfer member 230 as shown in FIG. 4B. The folded diaper pant 101 may be fully folded (for example, the inner surface 132 of the first waist region 116 is in contact with the inner surface 132 of the second waist region 118) when the folded diaper pant 101 advances onto the receiving surface 246 of the transfer member 230. The transfer apparatus 220 may rotate the folded diaper pant 101 in the machine direction MD about a first axis of rotation 232. The transfer member 230 may advance the folded diaper pant 101 through the gap 210 between the transfer member 230 and the guide member 202 as shown in FIG. 5A.

Figure 5A:
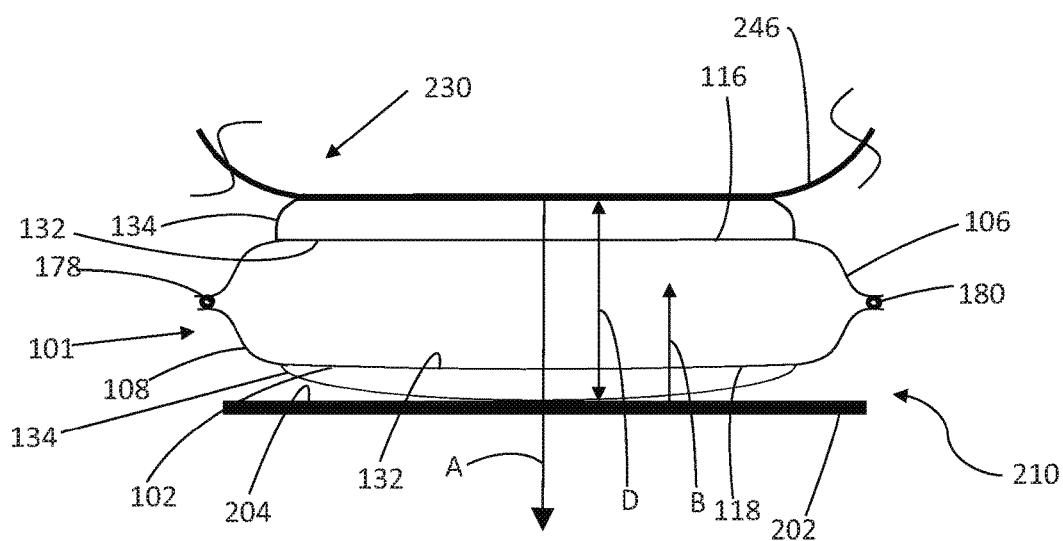
FIG. 5A is a schematic, sectional view of a folded diaper pant positioned in a gap between a guide member and a transfer member.
Figure 5B:
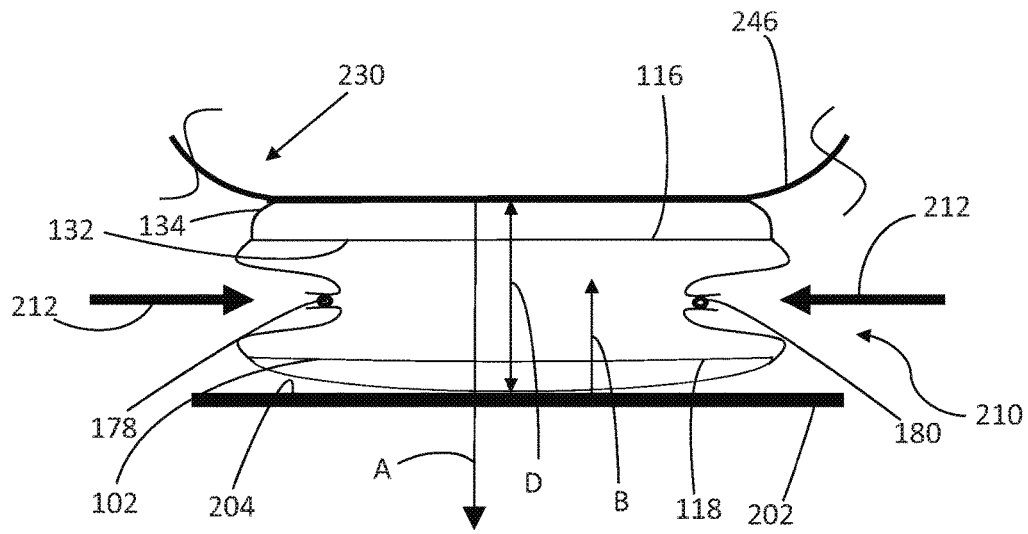
FIG. 5B is a schematic, sectional view of a folded diaper pant positioned in a gap between a guide member and a transfer member as side seam tuckers tuck first and second side seams into a chassis of the folded diaper pant.

Referring to FIGS. 4A, 4B, and 5A, as the transfer member 230 rotates about the first axis of rotation 232, centrifugal and/or gravitational forces may pull the second waist region 118 of the folded diaper pant 101 in a first direction, A, toward the guide surface 204. As the frame 228 rotates about the first axis of rotation 232, the transfer member 230 may concurrently rotate about the second axis of rotation 234. The guide surface 204 may converge towards the receiving surface 246 of the transfer member 230 such that the inner surface 132 of the second waist region 118 moves in a second direction, B, toward the first waist region 116 as the folded diaper pant 101 advances through the gap 210. As shown in FIG. 5B, and as discussed in more detail below, side seam tuckers 212 may be used to tuck the first and second side seams 178 and 180 as the second waist region 118 is positioned away from the first waist region 116. As the guide surface 204 converges toward the receiving surface 246, the second waist region 118 may move in the section direction, B, toward the first waist region 116, thereby holding the first and second side seams 178, 180 tucked into the chassis 102 of the folded diaper pant 101. As shown in FIG. 4B, the folded diaper pant 101 may advance from the gap 210 and onto the second carrier apparatus 238. Vacuum may be intermittently interrupted to remove the folded diaper pant 101 from the receiving surface 246 of the transfer member 230.

Figure 6:
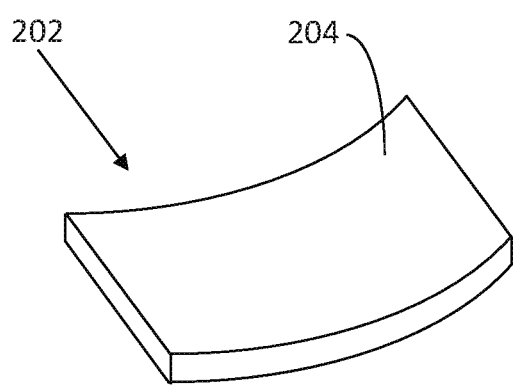
FIG. 6 is a schematic, perspective side view of an exemplary guide member.

As shown in FIG. 6, the guide member 202 includes a guide surface 204. With reference to FIG. 4A, the shape of the guide surface 204 may correspond with the shape of the receiving surface 246 of the transfer member 230. For example, the guide surface 204 may be curved, such as shown in FIG. 4A, to match the curved shape of the receiving surfaces 246. While it is shown that the guide surface 204 has a curved shape, it is to be appreciated that the guide surface 204 may be configured to have various other shapes. The guide member 202 may be stationary relative to the frame 228. In some exemplary configurations, the guide member 202 may be connected with the frame 228. It is to be appreciated that the guide member 202 may be connected with to the frame 228 in various ways.

Referring to FIGS. 5A and 6, the guide surface 204 may be configured to minimize the coefficient of friction between the guide surface 204 and the folded diaper pant 101. Exemplary guide surfaces include low-coefficient of friction plasma coating, polished steel, and polytetrafluoroethylene. In some configurations, the coefficient of friction between the guide surface 204 and the folded diaper pant 101 may be in the range of about 0.2 to about 0.35.

Figure 7:
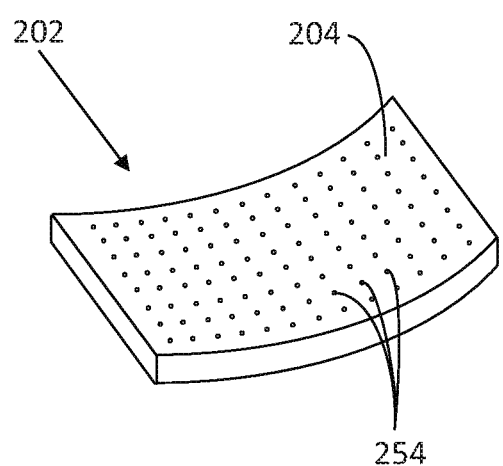
FIG. 7 is a schematic, perspective side view of an exemplary guide member having apertures in a guide surface.

In some exemplary configurations, with reference to FIG. 5A, the coefficient of friction between the guide surface 204 and the folded diaper pant 101 may be further reduced by applying a positive pressure to the outer surface 134 of the second waist region 118 of the folded diaper pant 101. As shown in FIG. 7, the guide surface 204 may include a plurality of apertures 254. The apertures 254 may be used to apply a positive pressure to the folded diaper pant as the folded diaper pant advances adjacent to the guide member 202. With reference to FIGS. 4B and 5A, the positive pressure helps to reduce the contact between the folded diaper pant 101 and the guide surface 204 as the folded diaper pant 101 advances in the machine direction MD. As a result of applying a positive pressure to the folded diaper pant 101, the coefficient of friction may be reduced between the folded diaper pant 101 and the guide surface 204. In turn, the guide member 202 may limit the movement of the second waist region 118 in the first direction, A, without inhibiting the advancement of the folded diaper pant 101 in the machine direction MD. It is to be appreciated that the apertures 254 shown in FIG. 7 may be arranged in various configurations on the guide surface 204. Applying a positive pressure to the folded diaper pant 101 may result in a coefficient of friction between the folded diaper pant 101 and the guide surface 204 of less than about 0.35.

Figure 8:
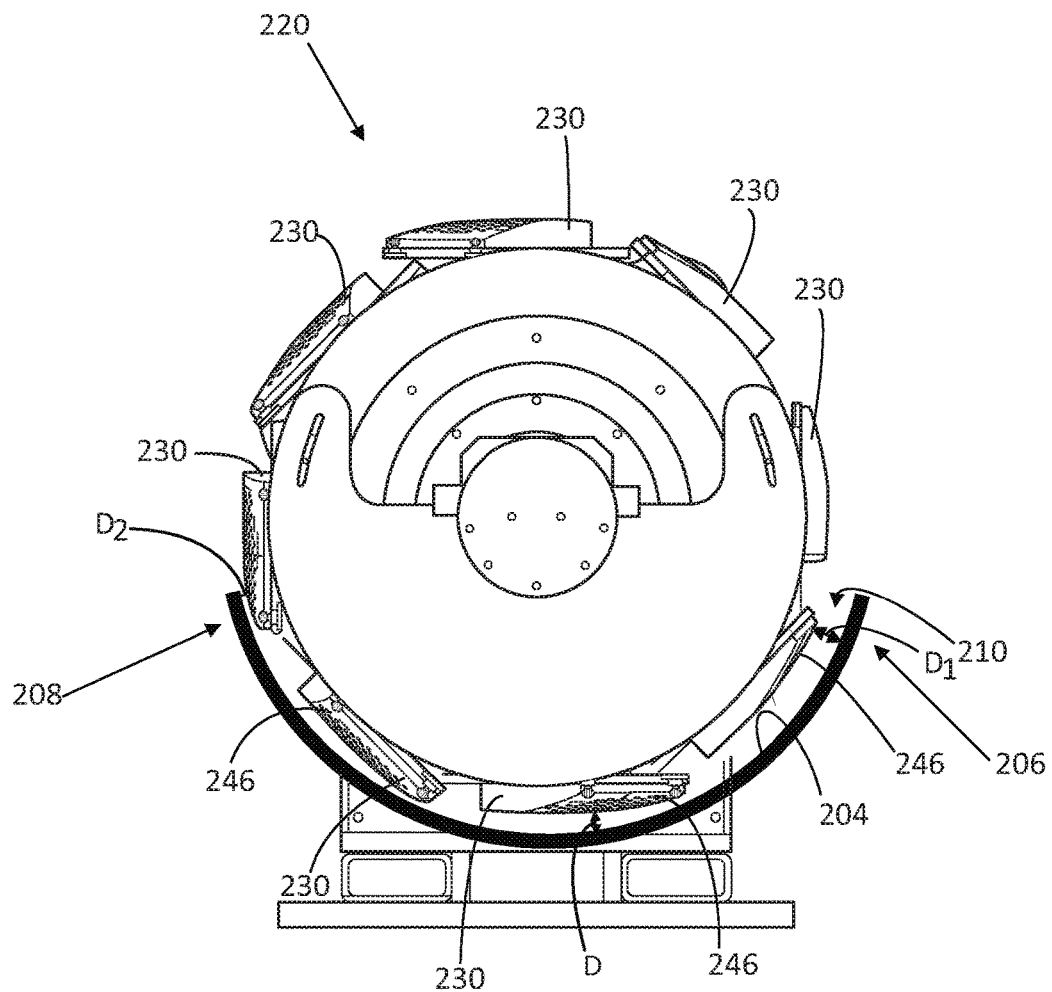
FIG. 8 is a schematic, side elevation view of a guide member locating adjacent to a transfer apparatus for guiding a folded diaper pant advancing in a machine direction.

As previously mentioned, the guide surface 204 may be configured or shaped to converge towards the receiving surface 246 of the transfer member 230. As such, the gap 210 between the receiving surface 246 and the guide surface 204 may become smaller as the transfer member 230 rotates around the first axis of rotation 232. For example, as shown in FIG. 8, the gap 210 may be defined by a minimum distance D between the receiving surface 246 and the guide surface 204. The receiving surface 246 may be located a first distance $D_1$ from the guide surface 204 when the transfer member 230 is relatively near the first end portion 206 of the guide member 202. Moreover, the receiving surface 246 may be located a second distance $D_2$ from the guide surface 204 when the transfer member 230 is relatively near the second end portion 208 of the guide member 202. The second distance $D_2$ may be less than the first distance $D_1$. As a result, the diaper pant may be fully folded when the folded diaper pant is located relatively near the second end 208 of the guide member 202. In some exemplary configurations, the minimum distance D from the receiving surface 246 to the guide surface 204 may gradually decrease from the first end portion 206 of the guide member 202 to the second end portion 208 of the guide member 202. However, it is to be appreciated that in some exemplary configurations the minimum distance D between the receiving surface 246 to the guide surface 204 may be constant for a length of the guide member 202 and then may gradually decrease.

Figure 9A:
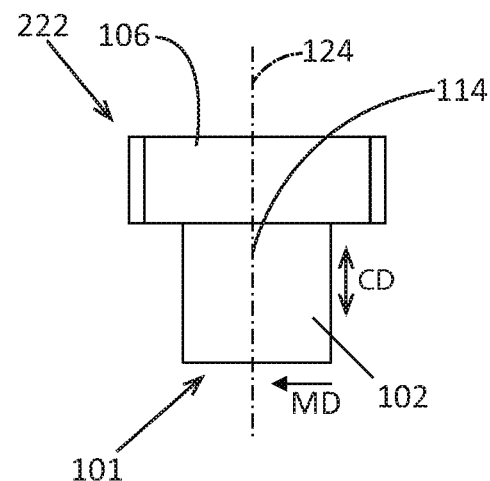
FIG. 9A is a schematic, plan view of a folded diaper pant in a first orientation.
Figure 9B:
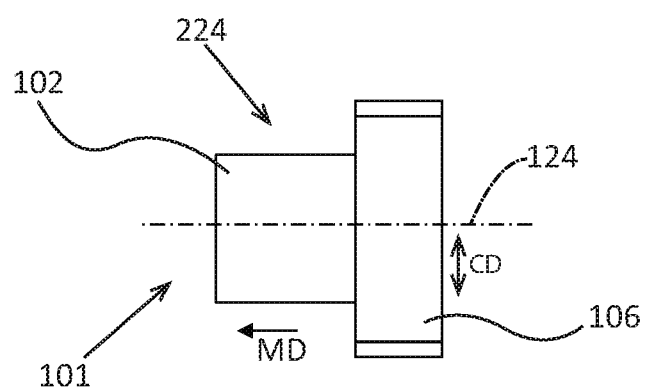
FIG. 9B is a schematic, plan view of a folded diaper pant in a second orientation.

Referring back to FIG. 4B, the folded diaper pant 101 may transfer from the first carrier apparatus 236 to the transfer apparatus 220 in a first orientation. As shown in FIG. 9A, in the first orientation 222, the longitudinal centerline 124 of the folded diaper pant 101 extends in the cross direction CD. The transfer apparatus 220 advances the folded diaper pant 101 in the machine direction MD about the first axis of rotation 232 while the transfer member 230 rotates the folded diaper pant 101 about the second axis of rotation 234. The folded diaper pant 101 then advances through the gap 210 between the transfer member 230 and the guide member 202. As shown in FIGS. 4B and 5A, centrifugal and/or gravitational forces pull the second waist region 118 of the folded diaper pant 101 in the first direction, A, toward the guide member 202. The guide member 202 limits movement of the second waist region 118 in the first direction, A, while allowing the folded diaper pant 101 to advance in the machine direction MD with minimal frictional resistance between the folded diaper pant 101 and the guide surface 204. As the frame 228 continues rotating about the first axis of rotation 232, the minimum distance D decreases. As a result, the second waist region moves in the second direction, B, and the folded diaper pant 101 may fully fold (for example, the first waist region contacts the second waist region) before advancing from the gap 210 and onto the second carrier apparatus 238. The folded diaper pant 101 is in a second orientation as the folded diaper pant 101 advances onto the second carrier apparatus 238. In the second orientation 224, the longitudinal centerline 124 of the folded diaper pant 101 extends in the machine direction MD as shown in FIG. 9B.

Figure 10:
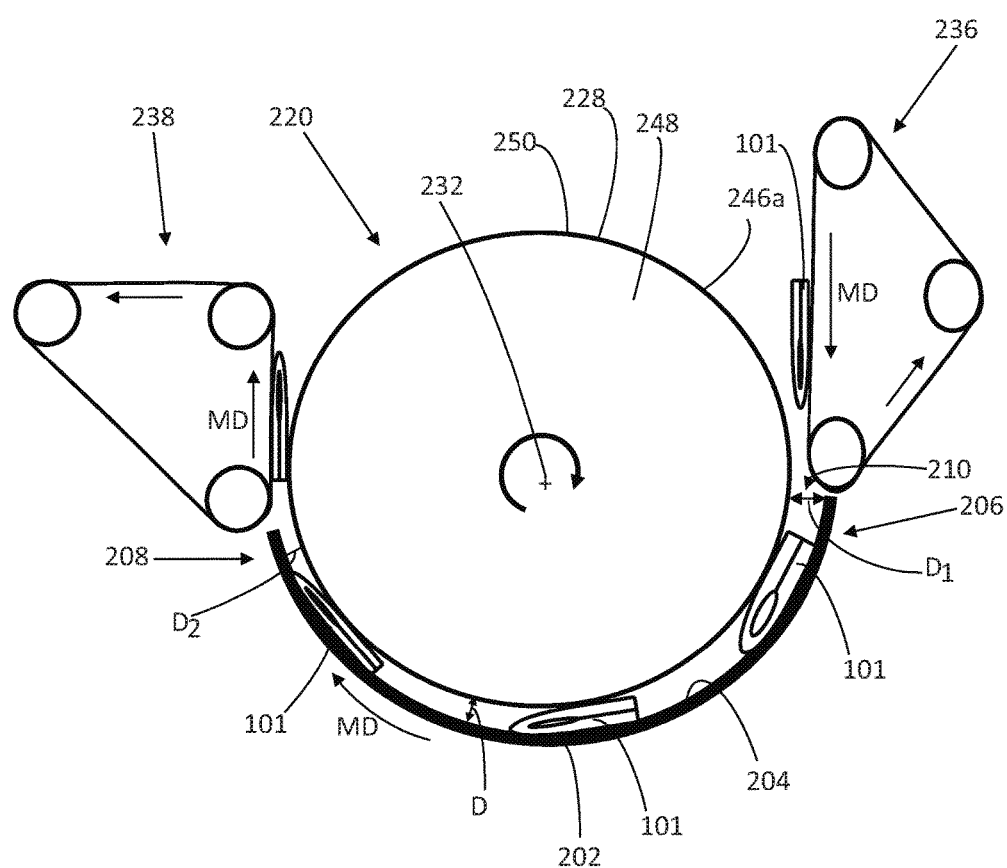
FIG. 10 is a schematic, side elevation view a transfer apparatus having a frame in the form of a drum.

The frame 228 of the transfer apparatus 220 may be configured in various different ways. For example, as shown in FIG. 10, the frame 228 may be configured as a drum 248. The drum 248 may include an outer circumferential surface 250 that forms a receiving surface 246a for advancing the folded diaper pants 101. The shape of the guide surface 204 may be configured to correspond with the curved outer circumferential surface 250 of the drum 248. The receiving surface 246a and the guide surface 204 are separated by a gap 210. The gap 210 is defined by a minimum distance D. The gap 210 may have a first distance $D_1$ at the first end portion 206 and a second distance $D_2$ at the second end portion 208, where the second distance $D_2$ is shorter than the first distance $D_1$. It is to be appreciated that the frame 228 may be configured in various other way for advancing the folded diaper pant in the machine direction MD; for example, the frame may comprise a conveyor or a series of rollers.

Figure 11A:
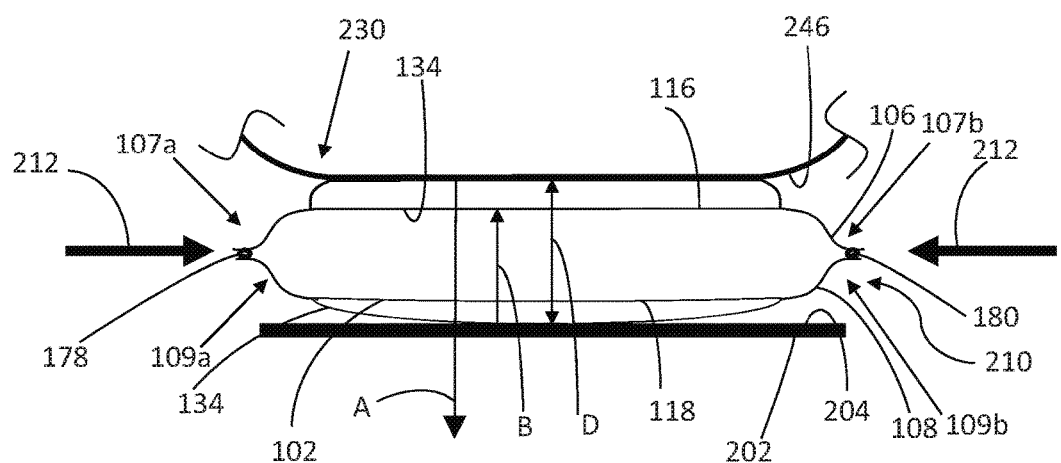
FIG. 11A is a schematic, sectional view of a folded diaper pant positioned in a gap between a transfer member and a guide member.

In some exemplary configurations, the first and second end regions of the first and second elastic belts, including the first and second side seams, may be tucked into the chassis of the folded diaper pant as the folded diaper pant is advanced through the gap between the transfer member and the guide member. As shown in FIG. 11A, the first and second end regions 107a, 109a, and 107b, 109b of the first and second elastic belts 106, 108 may be fully, laterally extended away from each other as the folded diaper pant 101 advances through the gap 210 between the receiving surface 246 and the guide surface 204. The minimum distance D between the guide surface 204 and the receiving surface 246 may be long enough to allow centrifugal and/or gravitational force to move the second waist region 118 away from the first waist region 116, side seam tuckers 212 may be used to push the first and second end regions 107a, 109a, and 107b, 109b of the first and second elastic belts 106, 108 into the chassis 102 of the folded diaper pant 101. Tucking the first and second side end regions 107a, 109a, and 107b, 109b of the first and second elastic belts 106, 108 into the chassis 102 creates longitudinal fold lines 166. As the folded diaper pant 101 advances through the gap 210, the guide member 202 converges toward the receiving surface 246 and the minimum distance D decreases. As a result, the second waist region 118 moves closer to the first waist region 116 and the first and second waist regions 116, 118 act to hold the first and second side seams 178, 180 in a tucked configuration between the first and second waist regions 116, 118.

Figure 11B:
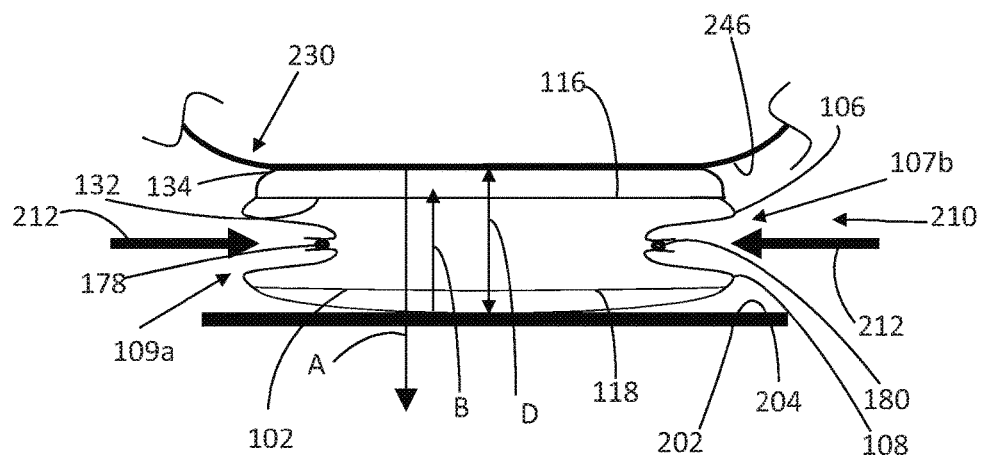
FIG. 11B is a schematic, sectional view of a folded diaper pant having side seams that are tucked into a chassis of the folded diaper pant using side seam tuckers.
Figure 11C:
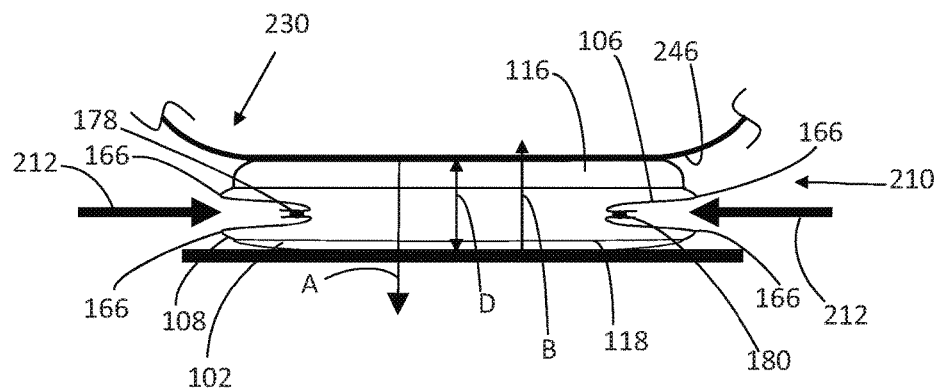
FIG. 11C is a schematic, sectional view of a folded diaper pant having side seams that are tucked into a chassis of the folded diaper pant using side seam tuckers.
Figure 12:
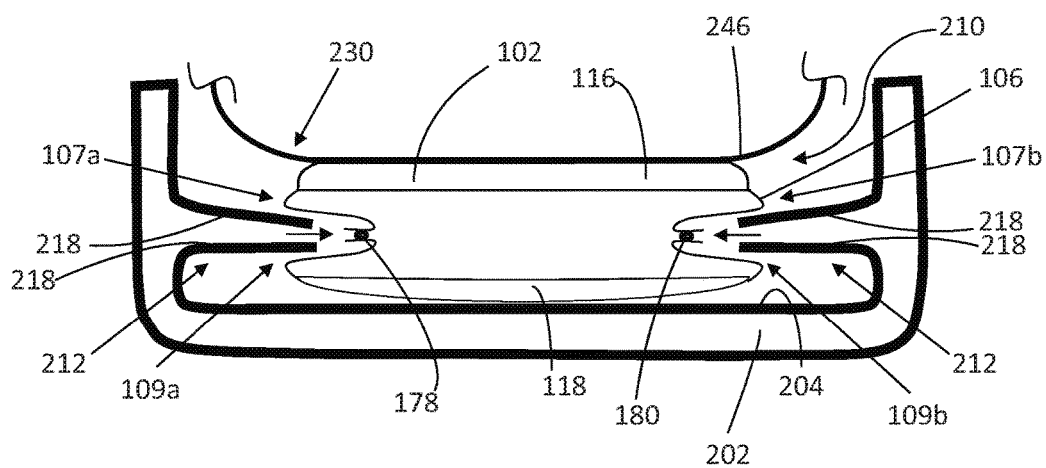
FIG. 12 is a schematic, sectional view of a folded diaper pant having side seams that are tucked into a chassis of the folded diaper pant using a guide member.

With continued reference to FIGS. 11A-11C, it is to be appreciated that the first and second end regions 107a, 109a and 107b, 109b of the first and second elastic belts 106, 108 may be tucked using various techniques. For example, the side seam tuckers 212 may be configured as air jets or rotating blades. Various methods and apparatuses for tucking side seams are disclosed in: U.S. Patent Publication No. US2011/0247747A1, published on Oct. 13, 2011, U.S. Patent Publication No. US2011/0251038A1, published Oct. 13, 2011; and U.S. Pat. Nos. 6,523,035 and 6,776,316. In some exemplary configurations, the side seam tuckers 212 may be integral with the guide member 202, such as shown in FIG. 12. The guide member 202 may be configured with side seam tuckers 212 in the form of tucking members 218 that direct the first and second end regions 107a, 109a and 107b, 109b into the chassis 102. The tucking members 218 may be adapted to apply positive air pressure to the first and second end regions 107a, 109a and 107b, 109b as shown in FIG. 12. In some exemplary configurations, positive air pressure may be applied through the apertures of the guide surface 204 and through the tucking members 218 of the guide member 202.

Figure 13:
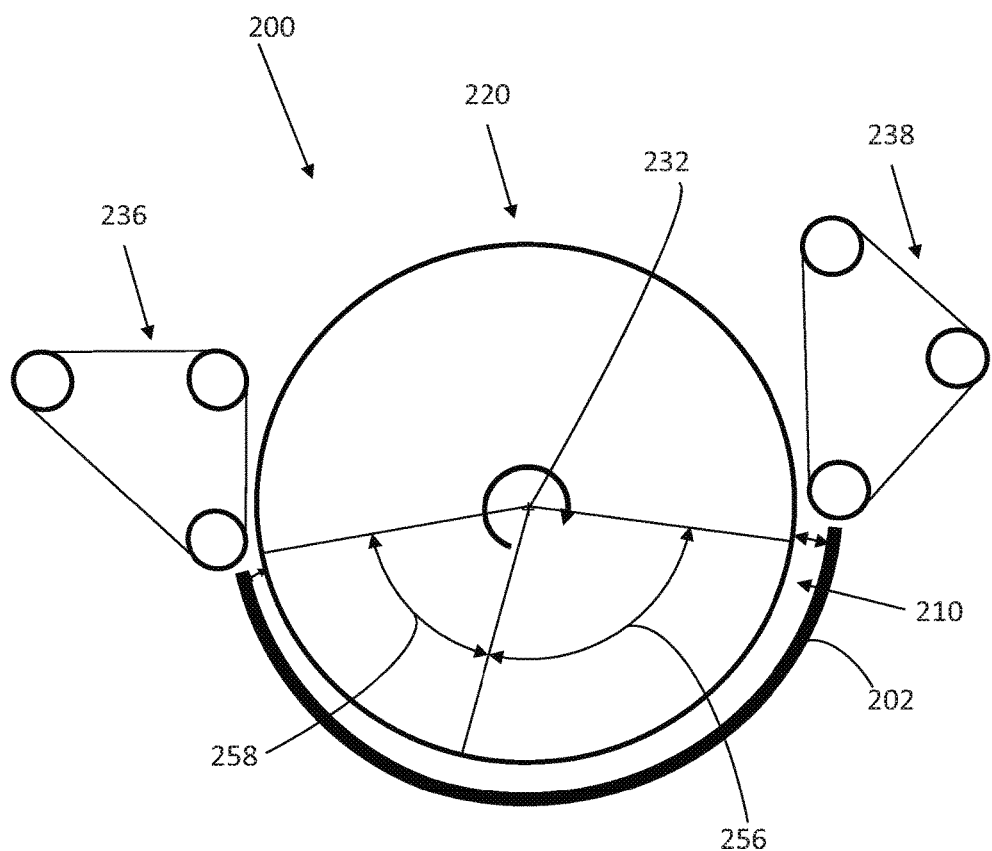
FIG. 13 is a schematic, side elevation view of a guide member located adjacent to a transfer apparatus having a rotating zone and a tucking zone.

In an exemplary configuration where the transfer apparatus 220 rotates the folded diaper pants 101 about the second axis of rotation 234, such as shown in FIG. 4B, the tucking process may occur after the folded diaper pant 101 is rotated from the first orientation 222 shown in FIG. 9A to the second, final orientation 224 shown in FIG. 9B. As shown in FIG. 13, the transfer apparatus 220 may be configured to have a rotating zone 256 and a tucking zone 258. It is to be appreciated that the rotating zone 256 and the tucking zone 258 may have various lengths. For example, the rotating zone 256 may be 90° and the tucking zone may be 60°. Once the folded diaper pant is rotated, the tucking process may start.

Figure 14:
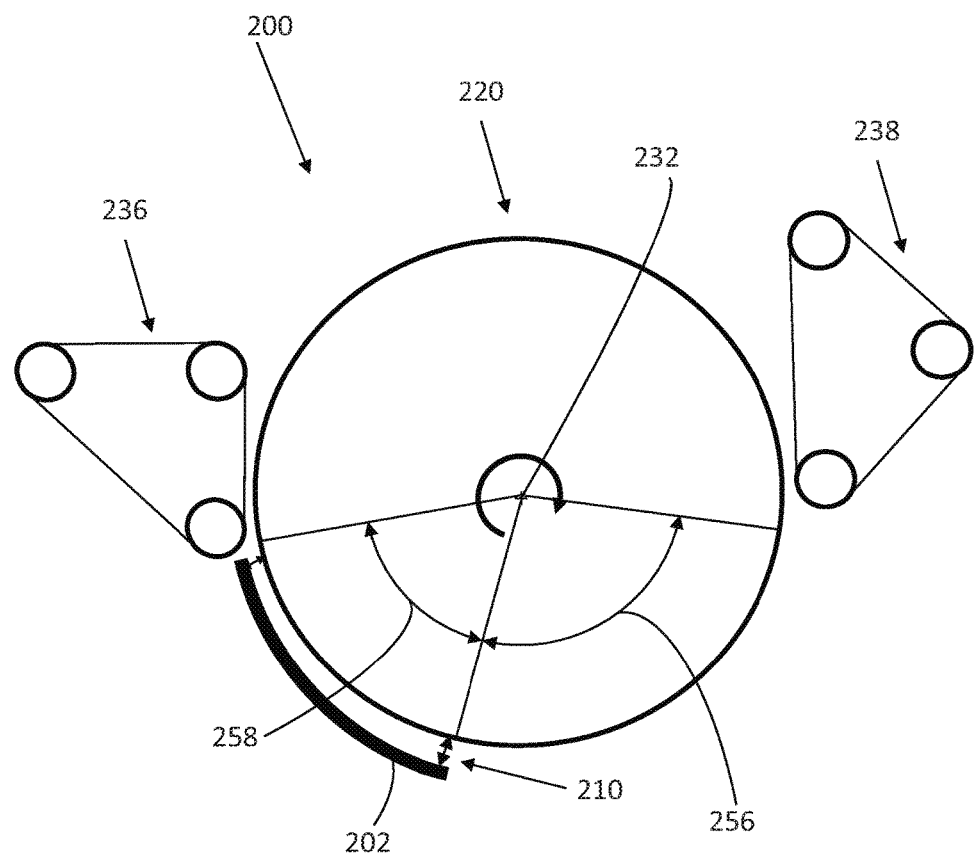
FIG. 14 is a schematic, side elevation view of a guide member located adjacent to a tucking zone of a transfer apparatus.

The guide member may be configured in various ways. As shown in FIG. 14, in some exemplary configurations, the transfer apparatus 220 may be configured to rotate the folded diaper pants before advancing the folded diaper pants through the gap 210 between the transfer member 230 and the guide member 202. As such, the guide member 202 may only extend along the tucking zone 258.

Figure 15:
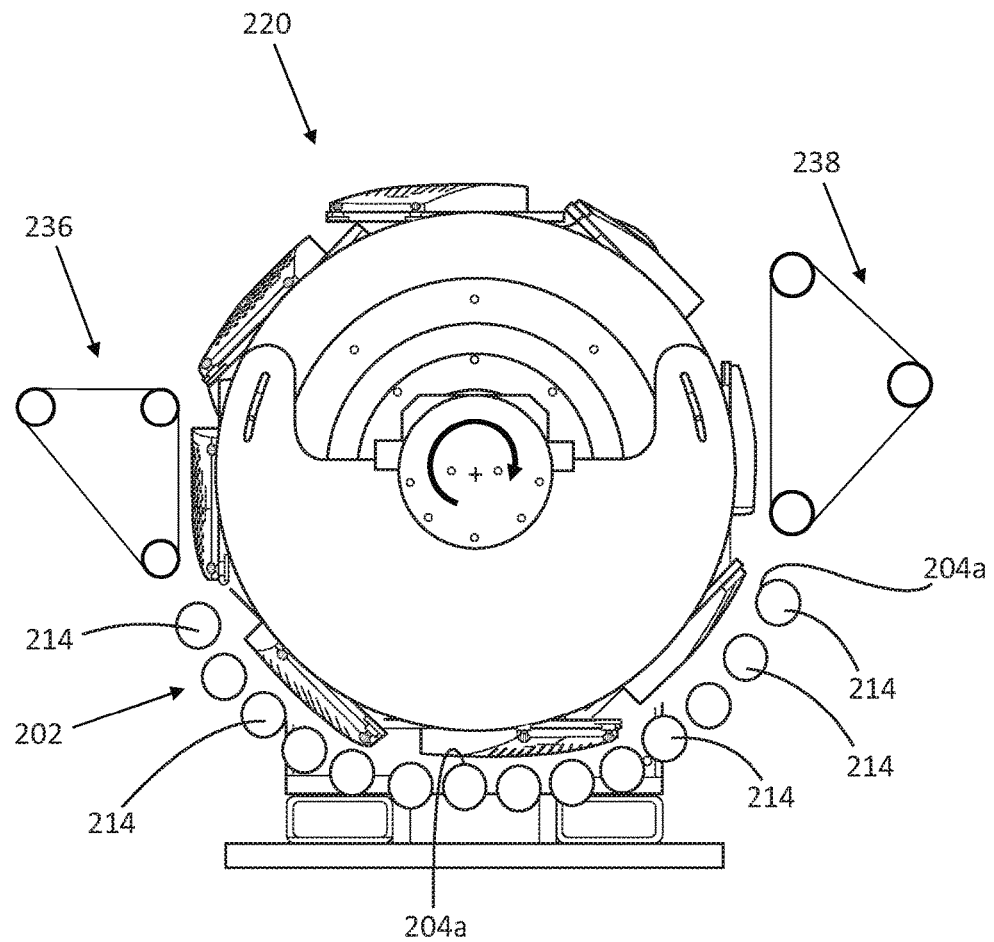
FIG. 15 is a schematic, side elevation view of a transfer apparatus located adjacent to a guide member comprising a plurality of rollers.
Figure 16:
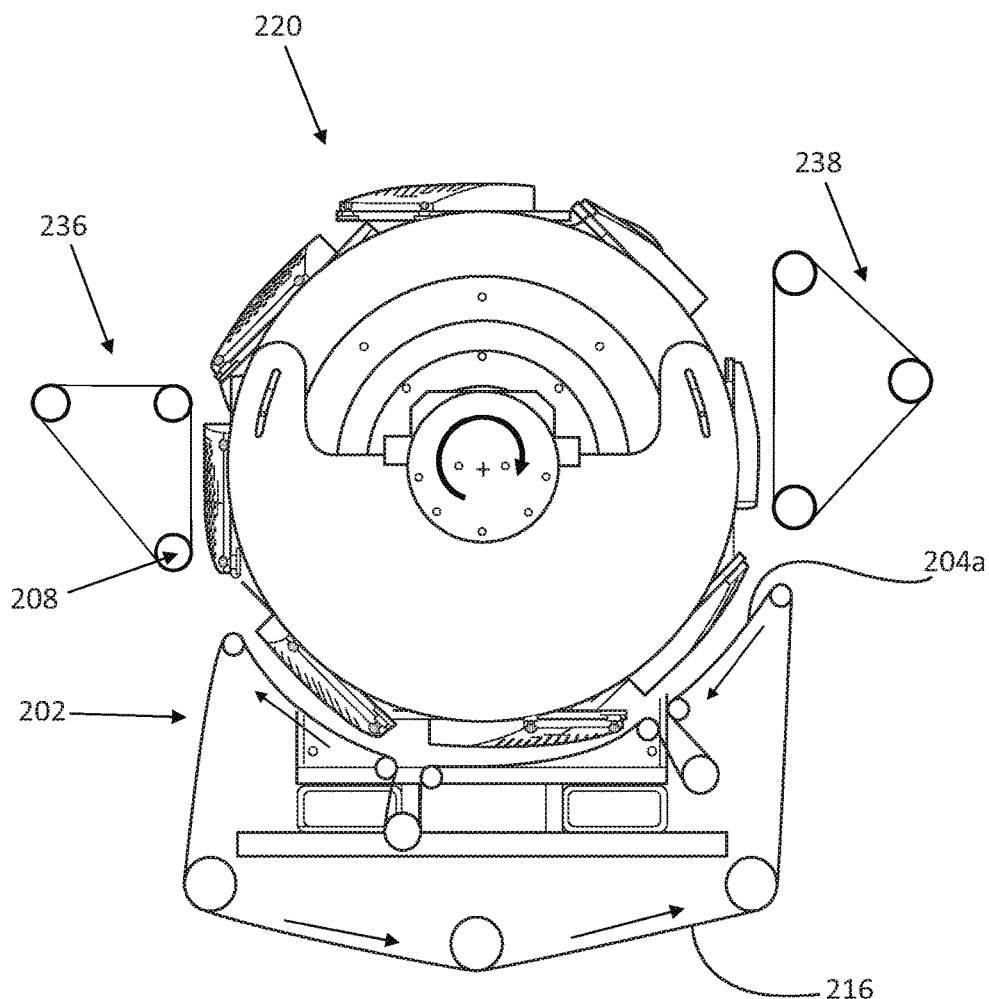
FIG. 16 is a schematic, side elevation view of a transfer apparatus located adjacent to a guide member comprising a conveyor.

In another exemplary configuration shown in FIG. 15, the guide member 202 may be configured as a series of rollers 214. In other exemplary configurations, such as shown in FIG. 16, the guide member 202 may be configured as a conveyor 216. It is to be appreciated that in a configuration where the guide member is configured as a series of rollers 214 or as a conveyor 216, the guide surface 204a may be moveable in order to guide the folded diaper pants in the machine direction MD. The guide surface 204a may be configured such that the coefficient of friction between the guide surface 204a and the folded diaper pant is relatively low. The rollers 214 and the conveyor 216 may be configured to apply a positive pressure to the folded diaper pant advancing through the gap 210.

This application is a continuation of U.S. application Ser. No. 14/038,828 filed on Sep. 27, 2013, which claims the benefit of U.S. Provisional Application No. 61/717,282 filed on Oct. 23, 2012, the entirety of which is incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for advancing an absorbent article, the absorbent article having a first waist region and a second waist region separated by a crotch region, wherein the absorbent article is folded such that the first waist region is in a facing relationship with the second waist region, wherein the absorbent article comprises a first elastic belt joined with the first waist region and a second elastic belt joined with the second waist region, wherein the first elastic belt is joined with the second elastic belt to form first and second side seams, the method comprising:
   advancing an absorbent article in a machine direction to a transfer apparatus, wherein the transfer apparatus comprises a frame and a transfer member rotatably connected with the frame, wherein the transfer member has a receiving surface;
   advancing an absorbent article onto the receiving surface of the transfer member;
   rotating the frame about a first axis of rotation to advance the absorbent article between the receiving surface and a guide member, wherein the guide member has a guide surface;
   separating the second waist region from the first waist region with centrifugal force;
   tucking the first and second side seams of the first and second elastic belts between the separated first and second waist regions; and
   guiding the second waist region into contact with the first waist region.

2. The method of claim 1, wherein the first waist region of the absorbent article contacts the receiving surface as the absorbent article advances on the transfer member and the second waist region is adjacent to the guide surface as the absorbent article advances between the receiving surface and the guide member.

3. The method of claim 2, wherein a gap is formed between the guide surface and the receiving surface, wherein the gap defines a first distance at a first end portion of the guide member and a second distance at a second end portion of guide member, wherein the second distance is shorter than the first distance.

4. The method of claim 1, further comprising concurrently rotating the transfer member about a second axis of rotation as the frame rotates about the first axis of rotation, wherein the second axis of rotation is orthogonal to the first axis of rotation.

5. The method of claim 4, further comprising rotating the absorbent article prior to tucking the first and second side seams of the first and second elastic belts.

6. The method of claim 1, wherein the guide surface has a coefficient of friction in the range of about 0.2 to about 0.35.

7. The method of claim 1, further comprising advancing the absorbent article from a first carrier apparatus to the transfer apparatus, wherein the first carrier apparatus comprises an endless belt.

8. The method of claim 1, further comprising advancing the absorbent article from the transfer apparatus to the second carrier apparatus, wherein the second carrier apparatus comprises an endless belt.

9. The method of claim 1, wherein the receiving surface is curved, wherein the guide surface is curved to correspond with the curved receiving surface.

10. The method of claim 1, further comprising directing an air jet at the first and second side seams of the first and second elastic belts.

11. A method for advancing an absorbent article, the absorbent article having a first waist region and a second waist region separated by a crotch region, wherein the absorbent article is folded such that the first waist region is in a facing relationship with the second waist region, wherein the absorbent article comprises a first elastic belt joined with the first waist region and a second elastic belt joined with the second waist region, wherein the first elastic belt is joined with the second elastic belt to form first and second side seams, the method comprising:
   advancing an absorbent article in a machine direction to a transfer apparatus, wherein the transfer apparatus comprises a frame and a transfer member rotatably connected with the frame, wherein the transfer member has a receiving surface;
   advancing an absorbent article onto the receiving surface of the transfer member;
   rotating the transfer apparatus about a first axis of rotation to advance the absorbent article between the receiving surface and a guide member, wherein the guide member has a guide surface;
   rotating the receiving surface about a second axis of rotation, wherein the first axis of rotation is orthogonal to the second axis of rotation;
   separating the second waist region from the first waist region with centrifugal force;
   tucking the first and second side seams of the first and second elastic belts between the separated first and second waist regions; and
   guiding the second waist region into contact with the first waist region.

12. An apparatus for controlling an absorbent advancing in a machine direction, the apparatus comprising:
   a frame rotatable about a first axis of rotation,
   a transfer member connected with the frame, the transfer member having a receiving surface;
   a guide member having a guide surface, and having a first end portion and a second end portion, the guide member positioned adjacent to frame so as to define a gap between the receiving surface and the guide surface, wherein the gap defines a first distance at the first end portion of the guide member and a second distance at the second end portion of the guide member, wherein the second distance is less than the first distance; and
   a side seam tucker located adjacent to the receiving surface.

13. The apparatus of claim 12, wherein the guide surface comprise a plurality of apertures, wherein the guide member is adapted to apply a positive pressure through the apertures.

14. The apparatus of claim 12, wherein the guide surface has a coefficient of friction in the range of about 0.2 to about 0.35.

15. The apparatus of claim 12, wherein the receiving surface is curved, wherein the guide surface is curved to correspond with the curved receiving surface.

16. The apparatus of claim 12, wherein the side seam tucker comprise an air jet.

17. The apparatus of claim 12, wherein the guide member is rotatable about a second axis of rotation, wherein the second axis of rotation is orthogonal to the first axis of rotation.

18. The apparatus of claim 12, wherein the side seam tucker is integral with the guide member.

19. The apparatus of claim 12, wherein the guide member comprises a series of rollers.

20. The apparatus of claim 12, wherein the guide member comprises a conveyor.

* * * * *